US009763966B2

(12) United States Patent
McKay et al.

(10) Patent No.: US 9,763,966 B2
(45) Date of Patent: *Sep. 19, 2017

(54) FLUOCINOLONE FORMULATIONS IN A BIODEGRADABLE POLYMER CARRIER

(71) Applicants:Warsaw Orthopedic, Inc., Warsaw, IN (US); Medtronic, Inc., Minneapolis, MN (US)

(72) Inventors: William F. McKay, Memphis, TN (US); Christopher M Hobot, Tonka Bay, MN (US); Danielle L. Biggs, Collierville, TN (US); Katara Shaw, Birmingham, AL (US); John Myers Zanella, Cordova, TN (US); Vanja Margareta King, Memphis, TN (US); Stephen Mark Cox, Inver Grove Heights, MN (US); Kathy L. Remsen, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/846,067

(22) Filed: Sep. 4, 2015

(65) Prior Publication Data

US 2016/0022704 A1    Jan. 28, 2016

Related U.S. Application Data

(62) Division of application No. 12/413,197, filed on Mar. 27, 2009, now Pat. No. 9,125,917.

(60) Provisional application No. 61/046,218, filed on Apr. 18, 2008.

(51) Int. Cl.
| | | |
|---|---|---|
| A61K 31/58 | (2006.01) |
| A61K 9/00 | (2006.01) |
| A61K 9/16 | (2006.01) |
| A61K 31/585 | (2006.01) |
| A61K 47/34 | (2017.01) |

(52) U.S. Cl.
CPC ............ *A61K 31/58* (2013.01); *A61K 9/0024* (2013.01); *A61K 9/1647* (2013.01); *A61K 31/585* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 4,624,255 A | 11/1986 | Schenck et al. |
| 4,863,457 A | 9/1989 | Lee |
| 5,522,844 A | 6/1996 | Johnson |
| 5,868,789 A | 2/1999 | Huebner |
| 5,922,340 A | 7/1999 | Berde et al. |
| 6,069,129 A | 5/2000 | Sandberg et al. |
| 6,179,862 B1 | 1/2001 | Sawhney |
| 6,248,345 B1 | 6/2001 | Goldenheim et al. |
| 6,287,588 B1 | 9/2001 | Shih et al. |
| 6,331,311 B1 | 12/2001 | Brodbeck et al. |
| 6,426,339 B1 | 7/2002 | Berde et al. |
| 6,428,804 B1 | 8/2002 | Suzuki et al. |
| 6,461,631 B1 | 10/2002 | Dunn et al. |
| 6,589,549 B2 | 7/2003 | Shih et al. |
| 6,630,155 B1 | 10/2003 | Chandrashekar et al. |
| 6,632,457 B1 | 10/2003 | Sawhney |
| 6,756,058 B2 | 6/2004 | Brubaker et al. |
| 6,773,714 B2 | 8/2004 | Dunn et al. |
| 6,974,462 B2 | 12/2005 | Sater |
| 7,144,412 B2 | 12/2006 | Wolf et al. |
| 7,166,570 B2 | 1/2007 | Hunter et al. |
| 7,220,281 B2 | 5/2007 | Lambrecht et al. |
| 7,229,441 B2 | 6/2007 | Trieu et al. |
| 7,235,043 B2 | 6/2007 | Gellman et al. |
| 7,318,840 B2 | 1/2008 | McKay |
| 7,329,259 B2 | 2/2008 | Cragg |
| 7,361,168 B2 | 4/2008 | Makower et al. |
| 7,367,978 B2 | 5/2008 | Drewry et al. |
| 2002/0009454 A1 | 1/2002 | Boone et al. |
| 2002/0090398 A1 | 7/2002 | Dunn et al. |
| 2003/0152637 A1 | 8/2003 | Chasin et al. |
| 2003/0204191 A1 | 10/2003 | Sater et al. |
| 2004/0072799 A1 | 4/2004 | Li et al. |
| 2004/0082540 A1 | 4/2004 | Hermida Ochoa |
| 2004/0214793 A1 | 10/2004 | Hermida Ochoa |
| 2005/0142163 A1 | 6/2005 | Hunter et al. |
| 2005/0186261 A1 | 8/2005 | Avelar et al. |
| 2005/0197293 A1 | 9/2005 | Mellis et al. |
| 2006/0073182 A1* | 4/2006 | Wong ................... A61K 9/0051 424/426 |
| 2006/0106361 A1 | 5/2006 | Muni et al. |
| 2006/0148903 A1 | 7/2006 | Burch et al. |
| 2006/0189944 A1 | 8/2006 | Campbell et al. |
| 2007/0156180 A1 | 7/2007 | Jaax et al. |

(Continued)

FOREIGN PATENT DOCUMENTS

WO    WO03005961 A2    1/2003

OTHER PUBLICATIONS

Kim et al. (International Journal of Pharmaceutics, 2005, 304, 165-177).*

(Continued)

*Primary Examiner* — Dennis Heyer
*Assistant Examiner* — Daniel M Podgorski

(57) ABSTRACT

Effective treatments of pain and inflammation are provided. Through the administration of an effective amount of fluocinolone at or near a target site, one can reduce, prevent or treat inflammation and pain and autoimmune disorders. In various embodiments, fluocinolone formulations may be provided within biodegradable polymers to reduce, prevent or treat sciatic pain and/or inflammation. In various embodiments, prevent transplant rejection for at least twenty-five days. In some embodiments, the pain relief can be for at least fifty days, at least one hundred days, at least one hundred and thirty-five days or at least one hundred and eighty days.

7 Claims, 11 Drawing Sheets

(56) References Cited

U.S. PATENT DOCUMENTS

| | | |
|---|---|---|
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2008/0091207 A1 | 4/2008 | Truckai et al. |

OTHER PUBLICATIONS

International Search Report for US Application No. PCT/US2009/041043 mailed Oct. 29, 2009.

QLT, Inc., Atrigel Drug Delivery System, www.qltinc.com, Jul. 2006.

* cited by examiner

| BATCH NUMBER | POLYMER | EXCIPIENT | DRUG LOAD (wt %) |
|---|---|---|---|
| 00178-27 | 100 DL 7E | 5% PEG 1500 | 1.71 |
| 00178-28 | 100 DL 7E | 5% PLURONIC F-68 | 1.79 |
| 00178-29 | 100 DL 7E | 7% 5050 DL 7A | 1.98 |
| 00178-30 | 100 DL 5E | 5% PEG 1500 | 1.97 |
| 00178-31 | 100 DL 5E | 5% PLURONIC F-68 | 1.82 |
| 00178-32 | 100 DL 5E | 7% 5050 DL 7A | 1.94 |
| 00178-33 | 100 DL 5E | 7% 5050 DL 7A | 1.98 |
| 00178-34 | 100 DL 7E |  | 1.92 |
| 00178-38 | 100 DL 5E | 10% PEG 1500 | 0.96 |
| 00178-39 | 100 DL 5E | 7% 5050 DL 7A, 5% PEG 1500 | 0.89 |
| 00178-40 | 100 DL 5E | 10% 5050 7A | 0.98 |
| 00178-41 | 100 DL 7E | 7% 5050 7A | 0.81 |
| 00178-42 | 100 DL 7E | 10% PEG 1500 | 0.85 |
| 00178-54 | 100 DL 5E | 10% PEG 1500 | 0.88 |

FIG. 1

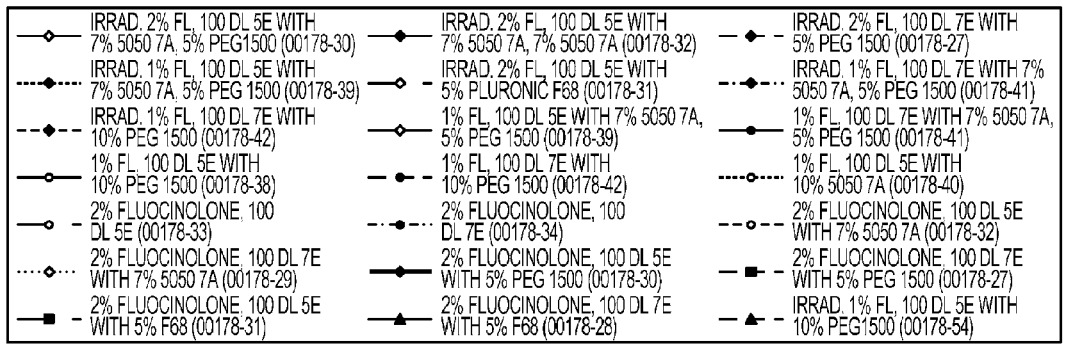
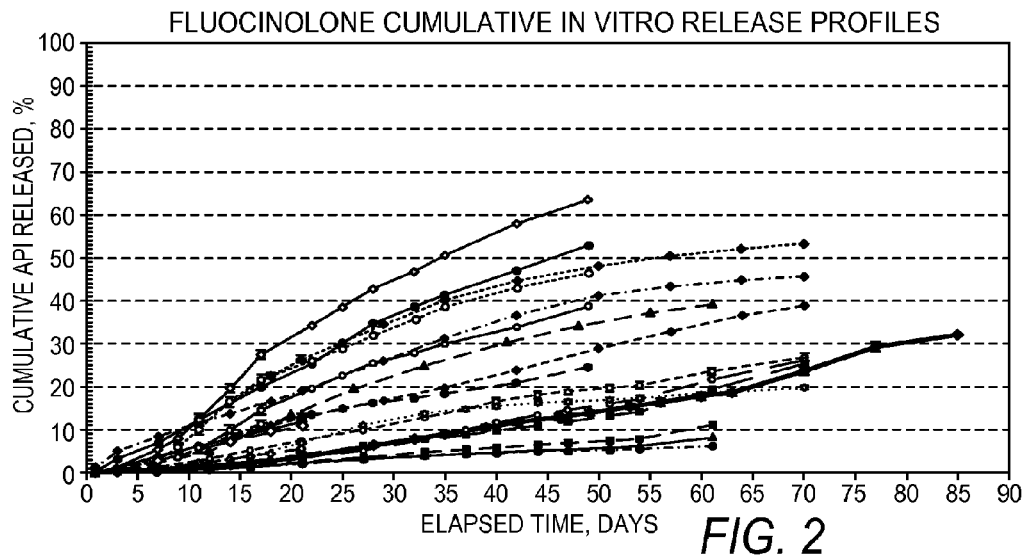
FIG. 2
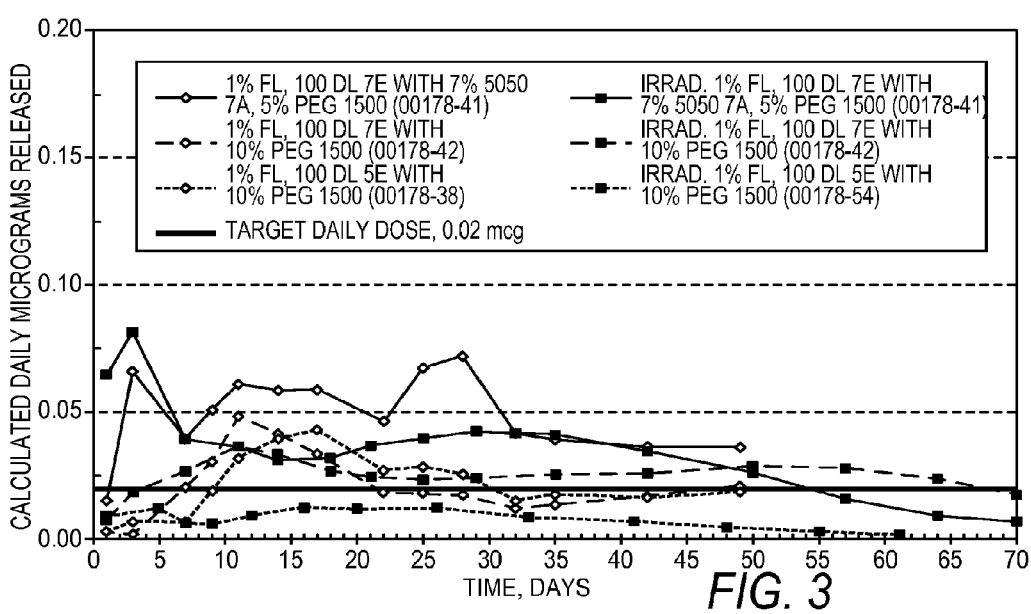
FIG. 3

FIG. 8

TABLE C

| NOTEBOOK ID | POLYMER TYPE | DRUG LOAD (Wt %) | EXCIPIENT | PELLET SIZE (L x Dia; mm) | PROCESSING | ELUTION |
|---|---|---|---|---|---|---|
| 13395-3-4 | 85/15 PLGA | 5% | mPEG | N/A | MELT PROCESSED | |
| 13395-4-1 | 85/15 PLGA | 10% | mPEG | 0.75 x 0.75 | MELT PROCESSED | X |
| 13395-4-2 | 85/15 PLGA | 15% | mPEG | 0.75 x 0.75 | MELT PROCESSED | X |
| 13395-4-3 | 85/15 PLGA | 20% | mPEG | 0.75 x 0.75 | MELT PROCESSED | X |
| 13395-35-5 | DL-PLA : 50/50 PLGA | 10% | mPEG | 0.8 x 0.8 | MELT PROCESSED | X |
| 13395-35-6 | 85/15 PLGA : 50/50 PLGA | 10% | mPEG | 0.8 x 0.8 | MELT PROCESSED | X |
| 13395-39-3 | 85/15 PLGA | 10% | mPEG | 0.8 x 0.8 | MELT PROCESSED | |
| 13395-42-3 | 85/15 PLGA | 5% | D-Sorbitol | 0.75 x 0.75 | MELT PROCESSED | X |
| 13395-42-4 | 85/15 PLGA | 5% | D-Sorbitol; mPEG | 0.75 x 0.75 | MELT PROCESSED | |
| 13395-42-5 | 85/15 PLGA | 5% | mPEG | 0.75 x 0.75 | MELT PROCESSED | |
| 13395-42-6 | 85/15 PLGA | 5% | D-Sorbitol | 0.75 x 0.75 | MELT PROCESSED | |
| 13395-48-1 | 85/15 PLGA | 5% | Maltodextrin; mPEG | 0.75 x 0.75 | MELT PROCESSED | X |
| 13395-53-1 | DL-PLA | 5% | mPEG | 1.0 x 1.0 | MELT PROCESSED | |
| 13395-53-2 | DL-PLA | 5% | D-Sorbitol; mPEG | 1.0 x 1.0 | MELT PROCESSED | |
| 13395-53-3 | DL-PLA | 5% | N/A | 1.0 x 1.0 | MELT PROCESSED | |
| 13395-53-4 | DL-PLA | 5% | D-Sorbitol | 1.0 x 1.0 | MELT PROCESSED | |
| 13395-54-1 | DL-PLA | 5% | Maltodextrin; mPEG | 1.0 x 1.0 | MELT PROCESSED | |
| 13395-54-3 | DL-PLA | 5% | 10% Maltodextrin; mPEG | 1.0 x 1.0 | MELT PROCESSED | |
| *13395-56-5 Task 31 | 85/15 PLGA | 20% | mPEG | 0.75 x 0.75 | MELT PROCESSED | X |
| 13395-59-1 | DL-PLA | 10% | 50% Maltodextrin | N/A | MELT PROCESSED | |
| 13395-63-6 | 85/15 PLGA | 20% | mPEG | 0.75 x 0.75 | MELT PROCESSED | X |
| 13395-66-1 | DL-PLA | 3% | 40% PEG (3350 MW) | N/A | MELT PROCESSED | |
| 13395-66-2 | DL-PLA | 3% | 20% PEG (3350 MW) | N/A | MELT PROCESSED | |
| 13395-72 | 85/15 PLGA | 2% | B - Cyclodextrin & mPEG | 0.75 x 0.75 | MELT PROCESSED | X |
| 13395-74 | 85/15 PLGA | 2% | B - Cyclodextrin | 0.75 x 0.75 | MELT PROCESSED | X |

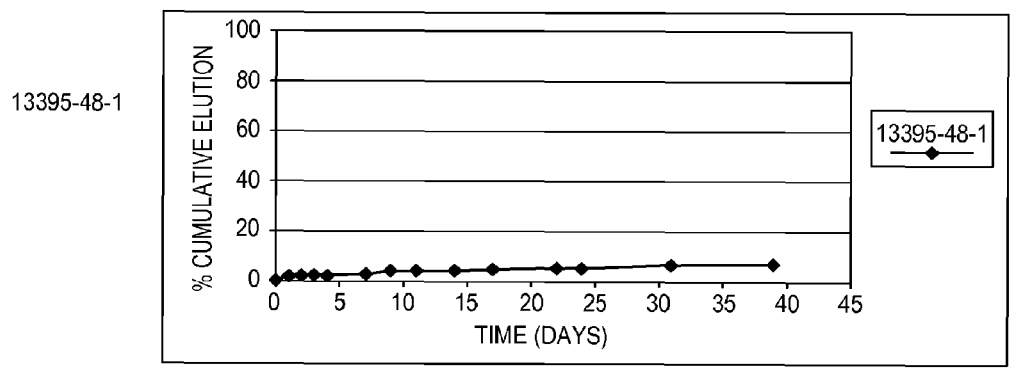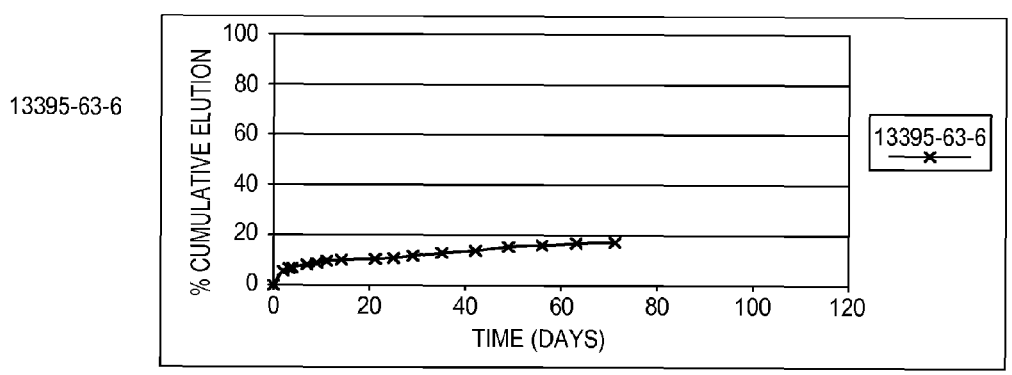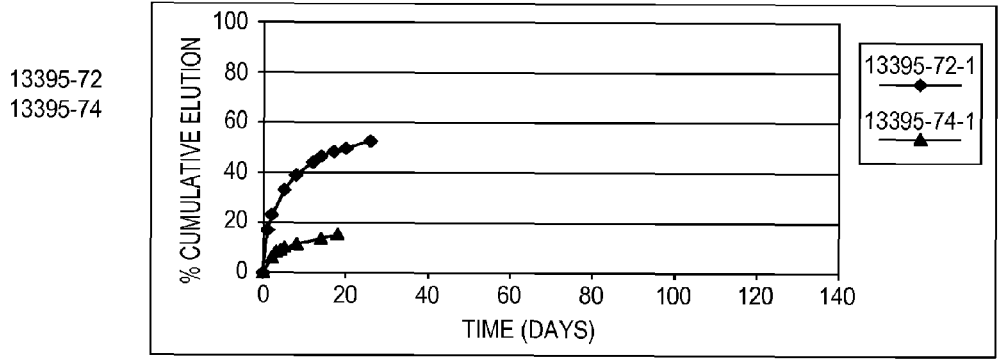
FIG. 10

FLUOCINOLONE FORMULATIONS IN A BIODEGRADABLE POLYMER CARRIER

This application is a divisional application of U.S. patent application Ser. No. 12/413,197 filed Mar. 27, 2009, entitled "Fluocinolone Formulations In A Biodegradable Polymer Carrier," which claims priority to and the benefit of U.S. Provisional Patent Application No. 61/046,218 filed Apr. 18, 2008 entitled "Fluocinolone Formulations In A Biodegradable Polymer Carrier." These entire disclosures are is hereby incorporated by reference into the present disclosure.

BACKGROUND

Inflammation is the result of a complex biological response of vascular tissues to harmful stimuli, such as pathogens, damaged cells, or irritants. It is part of an attempt by a patient to remove the injurious stimuli, as well as to initiate the healing process for the tissue. Due to an increased blood flow that accompanies this healing process, there is a rapid delivery of immune system cells thereby causing the patient to experience the swelling and redness that are associated with inflammation.

An inflammatory response may be initiated at the site of injury by endothelial cells that produce molecules that attract and detain inflammatory cells (e.g., myeloid cells such as neutrophils, eosinophils, and basophils). The inflammatory cells are then transported through the endothelial barrier into the surrounding tissue. The resulting accumulation of inflammatory cells, in particular neutrophils, is followed by generation of toxic oxygen particles and release of neutrophil granules that contain acid hydrolases and degradative enzymes such as proteases, elastase, and collagenase, which contribute to local tissue breakdown and inflammation. Neutrophils can also release chemoattractants and complement activators that amplify the inflammation.

Although the inflammatory response can play a role in the healing process by destroying, diluting, and isolating injurious agents as well as stimulating repair of the affected tissue, inflammatory responses can also be harmful, and indeed life-threatening. Five symptoms often characterize the inflammatory response: pain, redness, heat, swelling, and loss of function. For example, inflammation may result in leakage of plasma from the blood vessels. Although this leakage can have beneficial effects, it can also cause pain, and when uncontrolled lead to loss of function and, in severe cases, death. Anaphylactic shock, arthritis, and gout are among the conditions that are characterized by uncontrolled or inappropriate inflammation.

In certain situations, after injury or infection heals, proinflammatory activity persists. This, in turn, leaves sensory nerves carrying pain information to the brain to remain sensitized in the absence of injury or infection. Consequently, the patient experiences pain.

One particularly painful disease is sciatica. Sciatica is a chronic disease that often can be very debilitating and may take a terrible toll on those with the disease as well as their families, friends and caregivers. Sciatica is a very painful disease associated with the sciatic nerve which runs from the lower part of the spinal cord (the lumbar region), down the back of the leg and to the foot. Sciatica generally begins with a herniated disc, which later leads to local immune system activation. The herniated disc also may damage the nerve root by pinching or compressing it, leading to additional immune system activation in the area. There has been considerable interest in developing effective treatments for this painful disease, yet to date current treatments of sciatica are only partially effective.

Inflammation also has an immunological component, which can cause problems particularly in heterologous tissue or organ transplants. Transplant rejection occurs when the immune system of the recipient of a transplant attacks or rejects the tissue (or organ) that has been transplanted.

To prevent rejection, one strategy that is employed by the medical community to reduce the likelihood of transplant rejection is to use donated tissues from related individuals. A second strategy, which may be used in combination with the first strategy, is to use chemical compositions that suppress the immunological response that may lead to rejection of the donated tissue.

One compound that is known to reduce inflammation and/or immunological rejection of transplanted tissue is fluocinolone, which in its acetonide form ($C_{24}H_{30}F_2O_6$) has been administered topically as a cream in connection with hand transplants. It may also be referred to as 4b,12-Difluoro-6b-glycoloyl-5-hydroxy-4a,6a,8,8-tetramethyl-4a, 4b,5,6,6a,6b,9a,10,10a,10b,11,12-dodecahydro-2H-naphtho [2',1':4,5]indeno[1,2-d][1,3]dioxol-2-one or 6α-,9α-Difluoro-16α-hydroxyprednisolone 16,17-acetonide.

However, to date there is an unmet need to be able to reduce inflammation, pain, and/or immunological rejection utilizing sustained release fluocinolone.

SUMMARY

Compositions and methods are provided comprising fluocinolone or its pharmaceutically acceptable salts that are administered in order to reduce, prevent, or treat inflammation and/or pain. In various embodiments, the fluocinolone or its pharmaceutically acceptable salt may be administered to reduce, prevent or treat painful conditions such as sciatica. In various embodiments, the fluocinolone or its pharmaceutically acceptable salt may be administered to reduce, prevent or treat rejection of transplanted tissue.

These compositions and methods provided may be designed for long sustained release of the fluocinolone that has been internally placed. For example, these formulations and methods may be used in connection with sciatica. These compositions and methods may also be used in transplanted islet cells for diabetic patients and implanted at the same time that the donor islet cells are introduced.

According to one embodiment, there is a pharmaceutical formulation comprising: fluocinolone, wherein the fluocinolone or a pharmaceutically acceptable salt thereof comprises from about 0.5 wt. % to about 25 wt. % of the formulation, and at least one biodegradable polymer. The pharmaceutical composition may for example, be part of a drug depot. The drug depot may: (i) consist of only the fluocinolone (or one or more of its pharmaceutically acceptable salts) and the biodegradable polymer(s); or (ii) consist essentially of the fluocinolone (or one or more of its pharmaceutically acceptable salts) and the biodegradable polymer(s); or (iii) comprise the fluocinolone (or one or more of its pharmaceutically acceptable salts), the biodegradable polymer(s) and one or more other active ingredients, surfactants, excipients or other ingredients or combinations thereof. When there are other active ingredients, surfactants, excipients or other ingredients or combinations thereof in the formulation, in some embodiments, these other compounds or combinations thereof comprise less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %.

According to another embodiment, there is a pharmaceutical formulation comprising fluocinolone or a pharmaceutically acceptable salt thereof, wherein the fluocinolone or a pharmaceutically acceptable salt thereof comprises from about 0.5 wt. % to about 25 wt. % of the formulation, and at least one biodegradable polymer, wherein the at least one biodegradable polymer comprises poly(lactic-co-glycolic acid) or poly(orthoester) or a combination thereof, and said at least one biodegradable polymer comprises at least 80 wt. % of said formulation.

According to another embodiment, there is an implantable drug depot for reducing, preventing, or treating sciatica and/or tissue transplant rejection in a patient in need of such treatment, the implantable drug depot comprising fluocinolone or a pharmaceutically acceptable salt thereof in an amount from about 0.05 wt. % to about 25 wt. % of the formulation, and at least one biodegradable polymer.

According to another embodiment, there is an implantable drug depot for preventing rejection of transplanted tissue in a patient in need of such treatment, the implantable drug depot comprising fluocinolone or a pharmaceutically acceptable salt thereof in an amount of from about 0.5 wt. % to about 25 wt. % of the drug depot, and at least one biodegradable polymer, wherein the at least one biodegradable polymer comprises poly(lactic-co-glycolic acid) or poly(orthoester) or a combination thereof, and said at least one biodegradable polymer comprises at least 80 wt. % of said formulation.

According to another embodiment, there is an implantable drug depot for treating in a patient in need of such treatment, the implantable drug depot comprising fluocinolone or a pharmaceutically acceptable salt thereof in an amount of from about 0.5 wt. % to about 25 wt. % of the drug depot, and at least one polymer, wherein the at least one polymer comprises one or more of poly(lactide-co-glycolide), D-lactide, D,L-lactide, L-lactide, D,L-lactide-caprolactone, and D,L-lactide-glycolide-caprolactone.

According to another embodiment, there is a method of making an implantable drug depot, the method comprising combining a biocompatible polymer and a therapeutically effective amount of the fluocinolone or a pharmaceutically acceptable salt thereof and forming the implantable drug depot from the combination.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

FIG. 1 is a table of fourteen formulations that comprise fluocinolone.

FIG. 2 is a graphic representation of fluocinolone cumulative in vitro release profile as measured by the cumulative API release percentage.

FIG. 3 is a graphic representation of the calculated daily micrograms released for certain fluocinolone formulations.

FIG. 8 is a set of three graphs that depict in vitro elution data for a number of fluocinolone formulations.

FIG. 10 is a picture of fluocinolone implants 20 wt % 85/15 PLGA+10% mPEG and 1% wt fluocinolone 100 DL 7E+5% PEG/7% 50/50 PLGA 7A. The foreign and inflammatory material was not resorbed due to lack of inflammatory response mediated by fluocinolone implants. There was also no encapsulation due to attachment of cells such as fibroblasts.

Figure 4:
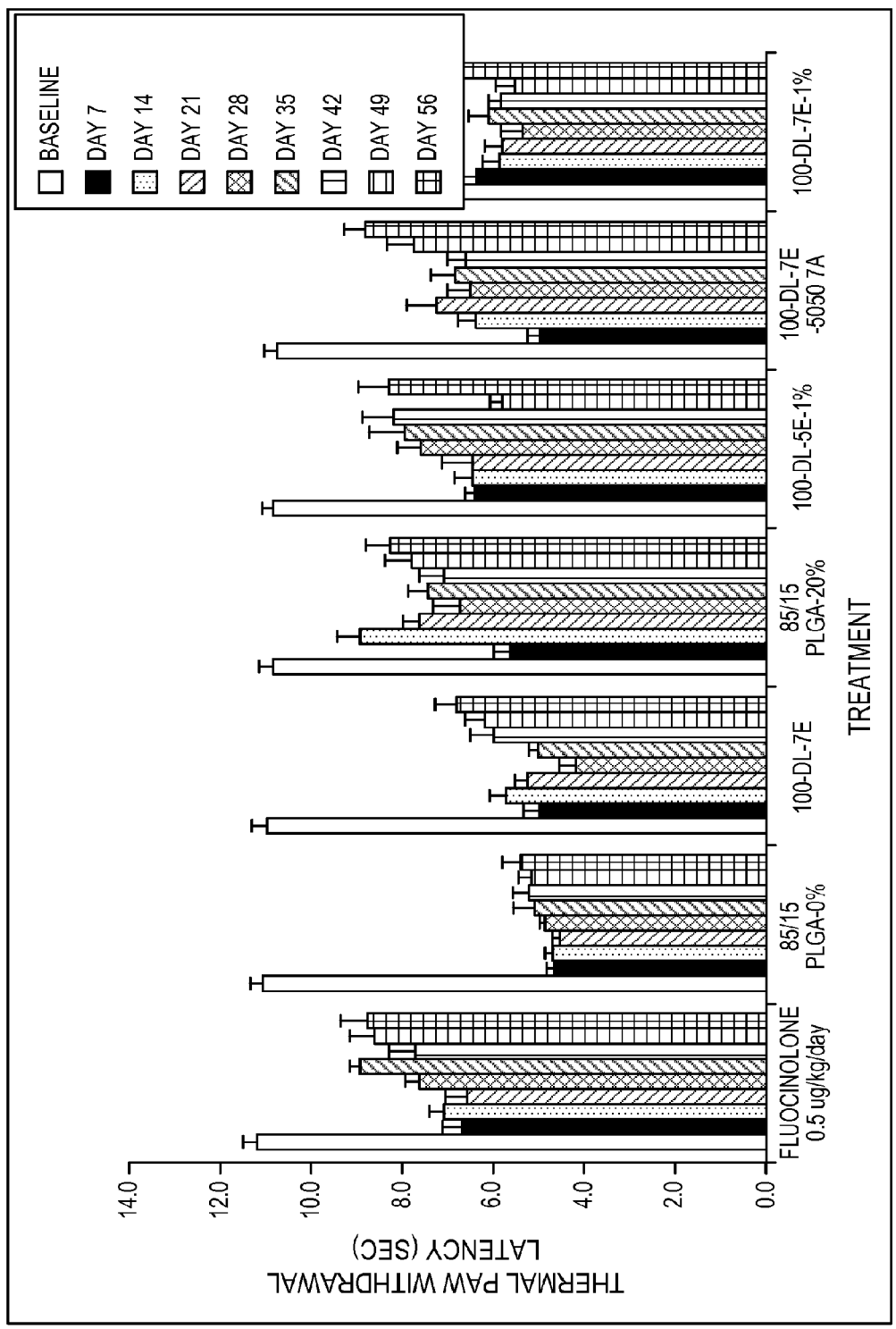
FIG. 4 is a bar graph that depicts the mechanical threshold as a percentage from baseline for the following administrations: fluocinolone 0.5 µg/kg/day subcutaneously, 85/15 PLGA-0%, 100-DL-7E, 85/15 PLGA-20%, 100-DL-5E-1%, 100-DL-7E-5050 7A and 100-DL-7E-1% at 8 days, 15 days, 22 days, 29 days, 36 days, 43 days, 50 days, and 57 days.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

A "drug depot" is the composition in which the fluocinolone is administered to the body. Thus, a drug depot may comprise a physical structure to facilitate implantation and retention in a desired site. The drug depot also comprises the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.01 cm to about 10 cm from the administration site and comprises fluocinolone. A drug depot may also include an infusion device holding the drug (e.g., pump) or pellet.

A "therapeutically effective amount" or "effective amount" is such that when administered, the drug results in alteration of the biological activity, such as, for example, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. The drug depot may comprise a pump that holds and administers the pharmaceutical. In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, etc.) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The two types of formulations (sustain release and immediate release) may be used in conjunction. For example, one can use a mixture of formulations, which provide different release profiles, either by use of different forms of the drug or by mixtures of different formulations of sustained release materials. The sustained release and immediate release may be in one or more of the same depots. In various embodiments, the sustained release and immediate release may be part of separate depots. For example a bolus or immediate release formulation of fluocinolone may be placed at or near the target site and a sustain release formulation may also be placed at or near the same site or be provided within the same formulation through a combination of different polymer matrices and/or drug forms. Thus, even after the bolus becomes completely accessible, the sustain release formulation would continue to provide the active ingredient for the intended tissue.

In various embodiments, the drug depot can be designed to cause an initial burst dose of therapeutic agent within the first twenty-four hours after implantation. "Initial burst" or "burst effect" or "bolus dose" refers to the release of therapeutic agent from the depot during the first twenty-four hours after the depot comes in contact with an aqueous fluid (e.g., synovial fluid, cerebral spinal fluid, etc.). The "burst effect" is believed to be due to the increased release of therapeutic agent from the depot. In alternative embodiments, the depot (e.g., gel) is designed to avoid this initial burst effect.

"Treating" or "treatment" of a disease or condition refers to executing a protocol that may include administering one or more drugs to a patient (human, other normal or otherwise or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient. Some conditions of pain and/or inflammation include chronic conditions, such as for example, rheumatoid arthritis, osteoarthritis, sciatica, carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, tissue or organ transplant rejection or the like. "Reducing inflammation or tissue or organ rejection" includes a decrease in inflammation and/or rejection and does not require complete alleviation of signs or symptoms of inflammation or rejection, and does not require a cure. In various embodiments, reducing inflammation or tissue or organ rejection includes even a marginal decrease in inflammation and/or tissue or organ rejection.

The term "pain" includes nociception and the sensation of pain, both of which can be assessed objectively and subjectively, using pain scores and other methods well-known in the art. In various embodiments, pain may include allodynia (e.g., increased response to a normally non-noxious stimulus) or hyperalgesia (e.g., increased response to a normally noxious or unpleasant stimulus), which can in turn be thermal or mechanical (tactile) in nature. In some embodiments, pain is characterized by thermal sensitivity, mechanical sensitivity and/or resting pain. In other embodiments, pain comprises mechanically-induced pain or resting pain. In still other embodiments, the pain comprises resting pain. The pain can be primary or secondary pain, as is well-known in the art. Exemplary types of pain reducible, preventable or treatable by the methods and compositions disclosed herein include, without limitation, lower back pain, neck pain, leg pain, radicular pain, or abdominal pain from abdominal surgery, and neuropathic pain of the arm, neck, back, lower back, leg, and related pain distributions resulting from disk or spine surgery.

"Localized" delivery includes delivery where one or more drugs are deposited within a tissue, for example, a nerve root of the nervous system or a region of the brain, or in close proximity (within about 10 cm, or preferably within about 5 cm, for example) thereto.

"Sciatica" is an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area. In various embodiments, the steroid may be used to reduce, treat, or prevent sciatic pain and/or inflammation by locally administering the statin at one or more target tissue sites (e.g., nerve root, dorsal root ganglion, focal sites of pain, at or near the spinal column, etc.).

The term "mammal" refers to organisms from the taxonomy class "mammalian," including but not limited to humans, other primates such as chimpanzees, apes, orangutans and monkeys, rats, mice, cats, dogs, cows, horses, etc.

The term "rejection" refers to the autoimmune response of an organism that enables an organism to recognize and then attempt to destroy foreign organisms such as bacteria or foreign tissue that have been introduced through for example a transplant.

The phrase "release rate profile" refers to the percentage of active ingredient that is released over fixed units of time, e.g., mcg/hr, mcg/day, 10% per day for ten days, etc. As persons of ordinary skill know a release rate profile may, but need not, be linear.

The term "solid" is intended to mean a rigid material, while "semi-solid" is intended to mean a material that has some degree of flexibility, thereby allowing the depot to bend and conform to the surrounding tissue requirements.

"Targeted delivery system" provides delivery of one or more drugs depots, gels or depots dispersed in the gel having a quantity of therapeutic agent that can be deposited at or near the target site as needed.

The present methods and compositions may suitably be used in the reduction, prevention, or treatment of a wide variety of immune mediated disorders. The term "immune mediated disorder" as used in here, refers to undesired immune reaction or pathology that is mediated or partially mediated by a cell of the lymphoid lineage (including T lymphocytes, B Lymphocytes) or myeloid lineage (including granulocytes, macrophages and monocytes) and which is detrimental to the patient in which it occurs. Such undesired immune reactions or pathologies may be mediated by T lymphocytes or are multifactorial, e.g. chronic inflammatory diseases, including autoimmune diseases, immune pathologies induced by infectious agents, immune reactions by or against allografts, atopic responses, allergic reactions and immunoproliferative disorders. These comprise chronic inflammatory diseases, including, but not limited to autoimmune diseases, such as multiple sclerosis, rheumatoid arthritis, osteoarthritis, insulin dependent diabetes (type I diabetes), systemic lupus erythrematosis and psoriasis, immune pathologies induced by infectious agents, such as helminthic (e.g., leishmaniasis) and certain viral infections, including HIV, and bacterial infections, including Lyme disease, tuberculosis and lepromatous leprosy, tissue transplant rejection, graft versus host disease and atopic conditions, such as asthma and allergy, including allergic rhinitis, gastrointestinal allergies, including food allergies, eosinophilia, conjunctivitis or glomerular nephritis.

The term "tissue" refers to any body tissue or organ from or within an organism, including but not limited to blood vessel tissue, pancreatic tissue, liver tissue, skin tissue, kidney tissue, heart tissue, bone, lung, bone marrow, etc.

The term "transplant" means insertion of cells or tissue from a first source, (e.g., organism or artificial source), which may also be referred to as a donor, into a second source, which also may be referred to as a recipient. The cells, tissue or organ may be from the same or different species (e.g., xenogenic). A transplant tissue may replace a damaged or otherwise deficient or defective tissue, or it may be inserted in an organism that is missing a particular tissue or the transplant tissue may be inserted into an organism without removing any of the recipient organism's tissues.

"Immunosuppressant" refers to a therapeutic agent that suppresses an autoimmune or immune response. For example, a steroid (e.g., fluocinolone). The steroid may be administered alone or in conjunction with other immunosuppressant drugs, such as for example, cyclosporin A, tacrolimus, sirolimus, or the like.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "PGA" refers to polyglycolide.

The abbreviation "G" can refer to glycolic acid.

The abbreviation "PEG" refers to poly(ethylene glycol).

The abbreviation "PLGA" refers to poly(lactide-co-glycolide).

The abbreviation "PLA" refers to polylactide.

The abbreviation "POE" refers to poly(orthoester).

The abbreviation "L" refers to lactic acid.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Fluocinolone

When referring to fluocinolone, unless otherwise specified or apparent from context it is understood that the inventors are also referring to pharmaceutically acceptable salts, pharmacologically-active derivatives of the fluocinolone or an active metabolite of the fluocinolone. As used herein, "pharmaceutically acceptable salts" refer to derivatives of the disclosed compounds (e.g., esters or amines) wherein the parent compound may be modified by making acidic or basic salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, or nitric acids; or the salts prepared from organic acids such as acetic, fuoric, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid. Pharmaceutically acceptable also includes the racemic mixtures ((+)-R and (−)-S enantiomers) or each of the dextro and levo isomers of the fluocinolone individually. The fluocinolone may be in the free acid or base form or be pegylated for long acting activity.

One common form of fluocinolone for administration to mammals is fluocinolone acetonide.

The fluocinolone or its pharmaceutically acceptable salt may be administered with a muscle relaxant. Exemplary muscle relaxants include by way of example and not limitation, alcuronium chloride, atracurium bescylate, baclofen, carbamate, carbolonium, carisoprodol, chlorphenesin, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may comprise other therapeutic agents in addition to the fluocinolone as well. These therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine.

Examples of therapeutic agents suitable for use also include, but are not limited to an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin or tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, bupivicaine, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

Other therapeutic agents that may be included in the fluocinolone depot include alpha receptor agonists (e.g., alpha-1 or alpha-2 receptor agonist or combinations thereof). Examples of alpha-1 adrenergic receptor agonists include, but are in no way limited to methoxamine, methylnorepinephrine, norepinephrine, metaraminol, oxymetazoline, phenylephrine, 2-(anilinomethyl)imidazolines, synephrine, or a combination thereof.

In some embodiments, the alpha adrenergic receptor agonist comprises an alpha-2 adrenergic receptor agonist, which acts as an analgesic and/or anti-inflammatory agent. Examples of alpha-2 adrenergic receptor agonists useful in the present application include, but are in no way limited to L-norepinephrine, clonidine, dexmetdetomidine, apraclonidine, methyldopa, tizanidine, brimonidine, xylometazoline, tetrahydrozoline, oxymetazoline, guanfacine, guanabenz, guanoxabenz, guanethidine, xylazine, moxonidine, mivazerol, rilmenidine, UK 14,304, B-HT 933, B-HT 920, octopamine or a combination thereof.

Other alpha adrenergic agonists include, but are not limited to, amidephrine, amitraz, anisodamine, apraclonidine, cirazoline, detomidine, epinephrine, ergotamine, etilefrine, indanidine, lofexidine, medetomidine, mephentermine, metaraminol, methoxamine, midodrine, naphazoline, norepinephrine, norfenefrine, octopamine, oxymetazoline, phenylpropanolamine, rilmenidine, romifidine, synephrine, talipexole, tizanidine, or a combination thereof.

The fluocinolone may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the depot will be a solid or semi-solid formulation comprised of a biocompatible material that can be biodegradable.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s). Non-biodegradable polymers include but are not limited to PVC and polyurethane.

In some embodiments, the drug depot may not be biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these types of drug depots may need to be removed after a certain amount of time.

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bioerodable, a bioabsorbable, and/or a biodegradable biopolymer that may provide immediate release, or sustained release of the fluocinolone. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect.

In various embodiments, the drug depot comprises poly (lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone, glycolide-caprolactone or a combination thereof.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the depot is to be placed in the spinal area, in various embodiments, the depot may comprise sterile preservative free material.

Some examples of excipients include, for example, mPEG (methoxypolyethyleneglycol), sorbitol, D-sorbitol, maltodextrin, cyclodextrin, B-cyclodextrin, PEG 1500, Pluronic F68, Pluronic F127, 5050 PLG 7A or combinations thereof. The excipients may be added in weight percentages from 0.001 wt % or 0.01 wt. % to 50 wt. %, 5 to 25 wt %, or 5 to 12 wt %.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film or sheet or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 2 mm. In various embodiments, the drug depot may have a layer thickness of from about 0.005 to 1.0 mm, such as, for example, from 0.05 to 0.75 mm.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads or particles. In various embodiments, the radiographic marker could be a spherical shape or a ring around the depot.

Gel

In various embodiments, the fluocinolone is administered in a gel (e.g., sprayable gel). The gel may have a pre-dosed viscosity in the range of about 1 to about 500 centipoise (cps), 1 to about 200 cps, or 1 to about 100 cps. After the gel is administered to the target site, the viscosity of the gel will increase and the gel will have a modulus of elasticity (Young's modulus) in the range of about $1\times10^4$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In one embodiment, a depot comprises an adherent gel comprising fluocinolone that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1\times10^4$ to about $3\times10^5$ dynes/cm$^2$, or $2\times10^4$ to about $2\times10^5$ dynes/cm$^2$, or $5\times10^4$ to about $1\times10^5$ dynes/cm$^2$. The post-dosed hardening gels (after delivery) may have a rubbery consistency and have a modulus of elasticity in the range of about $1\times10^4$ to about $2\times10^6$ dynes/cm$^2$, or $1\times10^5$ to about $7\times10^5$ dynes/cm$^2$, or $2\times10^5$ to about $5\times10^5$ dynes/cm$^2$. Other IV (inherent viscosity) ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polymer comprises 20 wt. % to 90 wt. % of the formulation.

In various embodiments, the molecular weight of the gel can be varied by many methods known in the art. The molecular weight of the polymer can be varied to regulate the release rate profile and/or delivery duration of the active ingredient. In general, as the molecular weight of the polymer increases, one or more of the following occurs: the burst index is lower, the release profile is flatter and/or the duration of delivery is longer. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time. By was of a non-limiting example, the polymer make up may comprise from 50:50 PLGA to 100 PLA and the molecular weight range may be from 0.45 to 0.8 dI/g.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition, which includes a low-molecular weight polymer. Polymeric gel formulations that include high molecular weight polymers, also tend to have a higher solution viscosity than a polymeric gel, which include a low-molecular weight polymer.

As persons of ordinary skill in the art are aware, when implantable elastomeric depot compositions having a blend of polymers with different end groups are used the resulting formulation will have a lower burst index and a regulated duration of delivery. For example, one may use polymers with acid and ester end groups. Additionally, by varying the comonomer ratio of the various monomers that form a polymer (e.g., the L/G (lactic acid/glycolic acid) or G/CL ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery.

Thus, depot compositions having a blend of polymers having different molecular weights, end groups and comonomer ratios can be used to create a depot formulation having a lower burst index and a regulated duration of delivery.

When the gel is designed to be a flowable gel, it can vary from low viscosity, similar to that of water, to high viscosity, similar to that of a paste, depending on the molecular weight and concentration of the polymer used in the gel. The viscosity of the gel can be varied such that the polymeric composition can be applied to a patient's tissues by any convenient technique, for example, by brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly (methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly(acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the gel, microspheres may be dispersed within the gel, the microspheres being loaded with fluocinolone. In one embodiment, the microspheres provide for a sustained release of the fluocinolone. In yet another embodiment, the gel, which is biodegradable, prevents the microspheres from releasing the fluocinolone; the microspheres thus do not release the fluocinolone until they have been released from the gel. For example, a gel may be deployed around a target tissue site (e.g., a nerve root). Dispersed within the gel are a plurality of microspheres that encapsulate the desired therapeutic agent. Certain of these microspheres degrade once released from the gel, thus releasing the fluocinolone.

Microspheres, much like a fluid, may disperse relatively quickly, depending upon the surrounding tissue type, and hence disperse the fluocinolone. In some situations, this may be desirable; in others, it may be more desirable to keep the fluocinolone tightly constrained to a well-defined target site. The present invention also contemplates the use of adherent gels to so constrain dispersal of the therapeutic agent. These gels may be deployed, for example, in a disc space, in a spinal canal, or in surrounding tissue.

Drug Delivery

It will be appreciated by those with skill in the art that the depot can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina. For transplanted tissues or organs, the depots may in various embodiments be placed at the organ site at the time of transplantation.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655 mm. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

In various embodiments, a kit is provided that may include additional parts along with the drug depot and/or medical device combined together to be used to implant the drug depot. The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may comprise an agent for radiographic imaging. Each tool may be separately packaged in a plastic pouch that is radiation sterilized. A cover of the kit may include illustrations of the implanting procedure and a clear plastic cover may be placed over the compartments to maintain sterility.

In various embodiments, a method for delivering a therapeutic agent into a site of a patient is provided, the method comprising inserting a cannula at or near a target tissue site and implanting the drug depot at the target site beneath the skin of the patient and spraying, brushing, dripping, injecting, or painting the gel in the target site to hold or have the drug depot adhere to the target site. In this way unwanted migration of the drug depot away from the target site is reduced or eliminated.

In various embodiments, to administer the gel having the drug depot dispersed therein to the desired site, first the cannula or needle can be inserted through the skin and soft tissue down to the target tissue site and the gel administered at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required, a subsequent layer or layers of gel can be applied on the drug depot to surround the depot and further hold it in place. Alternatively, the drug depot may be implanted first and then the gel placed around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

In various embodiments, when the target site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal.

The fluocinolone-based formulation of the present invention may be used as medicaments in the form of pharmaceutical preparations. The preparations may be formed in an administration with a suitable pharmaceutical carrier that may be solid or liquid and organic or inorganic, and placed in the appropriate form for parenteral or other administration as desired. As persons of ordinary skill are aware, known carriers include but are not limited to water, gelatine, lactose, starches, stearic acid, magnesium stearate, sicaryl alcohol, talc, vegetable oils, benzyl alcohols, gums, waxes, propylene glycol, polyalkylene glycols and other known carriers for medicaments.

Parenteral administration may additionally include, for example, an infusion pump that administers a pharmaceutical composition through a catheter, an implantable mini-pump that can be inserted at or near the target site, an implantable controlled release device or sustained release delivery system that can release a certain amount of the composition per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times, or at set intervals between deliveries.

Another embodiment of the present invention is directed to a method for treating a mammal that has received a tissue transplant, said method comprising administering a therapeutically effective amount of fluocinolone at a target site beneath the skin. The fluocinolone (or pharmaceutically acceptable salt) may for example be administered locally to the target tissue site as a drug depot.

In some embodiments, the fluocinolone is encapsulated in a plurality of depots comprising microparticles, microspheres, microcapsules, and/or microfibers.

In some embodiments there is a method for making an implantable drug depot. The method may comprise combining a biocompatible polymer and a therapeutically effective amount of fluocinolone or a pharmaceutically acceptable salt thereof and forming the implantable drug depot from the combination.

In some embodiments, the fluocinolone is suitable for parenteral administration. The term "parenteral" as used herein refers to modes of administration that bypass the gastrointestinal tract, and include for example, intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof. In some embodiments, the injection is intrathecal, which refers to an injection into the spinal canal (intrathecal space surrounding the spinal cord). An injection may also be into a muscle or other tissue.

In various embodiments, the drug depot comprising the fluocinolone can be made by combining a biocompatible polymer and a therapeutically effective amount of fluocinolone or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: fluocinolone and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: fluocinolone, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, fluocinolone may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This pre-compounded material is then mixed with therapeutic agent under conditions of lower temperature and mechanical shear, and the resulting mixture is shaped into the fluocinolone containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., fluocinolone), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of fluocinolone because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet) is cooled. Examples of cooling processes include air cooling and/or immersion in a cooling bath. In some embodiments, a water bath is used to cool the extruded depot. However, where a water-soluble therapeutic agent such as fluocinolone is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape. In various embodiments, fluocinolone is used and mixed or sprayed with the PLGA or PEG550 polymer, and the resulting depot may be formed by extrusion and dried.

In various embodiments, there is a pharmaceutical formulation comprising: fluocinolone, wherein the fluocinolone comprises from about 0.05 wt. % to about 25 wt. % of the formulation, and at least one biodegradable polymer. In some embodiments, the pharmaceutical the fluocinolone comprises from about 2 or 3 wt. % to about 20 wt. %, about 3 wt. % to about 18 wt. %, about 5 wt. % to about 15 wt. % or about 7.5 wt. % to about 12.5 wt. % of the formulation.

In some embodiments, the at least one biodegradable polymer comprises poly(lactic-co-glycolic acid) (PLA) or poly(orthoester) (POE) or a combination thereof. The poly(lactic-co-glycolic acid) may comprise a mixture of polyglycolide (PGA) and polylactide and in some embodiments, in the mixture, there is more polylactide than polyglycolide. In various embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In some embodiments, the biodegradable polymer comprises at least 50 wt. %, at least 60 wt. %, at least 70 wt. %, at least 80 wt. % of the formulation, at least 85 wt. % of the formulation, at least 90 wt. % of the formulation, at least 95 wt. % of the formulation; at least 97 wt. % of the formulation; at least 99 wt. % of the formulation; or at least 99.5 wt. % of the formulation. In some embodiments, the at least one biodegradable polymer and the fluocinolone are the only components of the pharmaceutical formulation.

In some embodiments, at least 75% of the particles have a size from about 10 micrometer to about 200 micrometers. In some embodiments, at least 85% of the particles have a size from about 10 micrometer to about 200 micrometers. In some embodiments, at least 95% of the particles have a size from about 10 micrometer to about 200 micrometers. In some embodiments, all of the particles have a size from about 10 micrometer to about 200 micrometers.

In some embodiments, at least 75% of the particles have a size from about 20 micrometer to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles have a size from about 20 micrometer to about 180 micrometers.

In some embodiments, there is a pharmaceutical formulation comprising: fluocinolone, wherein said fluocinolone comprises from about 0.05 wt. % to about 25 wt. % of the formulation, and at least one biodegradable polymer, wherein the at least one biodegradable polymer comprises poly(lactic-co-glycolic acid) or poly(orthoester) or a combination thereof, and said at least one biodegradable polymer comprises at least 80 wt. % of said formulation.

In some embodiments, there are methods for treating acute pain. These methods comprise: administering a pharmaceutical composition to an organism, wherein said pharmaceutical composition comprises from about 0.05 wt. % to about 25 wt. % of the formulation, and at least one biodegradable polymer. In some embodiments, the loading is from about 5 wt. % to about 10 wt. %. In some embodiments, the loading is from about 10 wt. % to about 20 wt. %. In various embodiments, the fluocinolone load is 0.5 wt %.

In some embodiment there is a higher loading of fluocinolone, e.g., at least 20 wt. %, at least 30 wt. %, at least 40 wt. %, at least 50 wt. %, at least 60 wt. %, at least 70 wt. %, at least 80 wt. %, or at least 90 wt. %.

A strategy of triangulation may be effective when administering these pharmaceutical formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In some embodiments, the formulations are slightly rigid with varying length, widths, diameters, etc. For example, certain formulations may have a diameter of 0.50 mm and a length of 4 mm. It should be noted that particle size may be altered by techniques such as mort and pestle, jet-drying or jet milling.

Fluocinolone is available from various pharmaceutical manufacturers. The dosage of fluocinolone may be from approximately 0.0005 to approximately 100 µg/day. Additional dosages of fluocinolone include from approximately 0.0005 to approximately 50 µg/day; approximately 0.0005 to approximately 25 µg/day; approximately 0.0005 to approximately 10 µg/day; approximately 0.0005 to approximately 5 µg/day; approximately 0.0005 to approximately 1 µg/day; approximately 0.005 to approximately 0.75 µg/day; approximately 0.0005 to approximately 0.5 µg/day; approximately 0.0005 to approximately 0.25 µg/day; approximately 0.0005 to approximately 0.1 µg/day; approximately 0.0005 to approximately 0.075 µg/day; approximately 0.0005 to approximately 0.05 µg/day; approximately 0.001 to approximately 0.025 µg/day; approximately 0.001 to approximately 0.01 µg/day; approximately 0.001 to approximately 0.0075 µg/day; approximately 0.001 to approximately 0.005 µg/day; approximately 0.001 to approximately 0.025 µg/day; and 0.002 to approximately 0.025 µg/day. In another embodiment, the dosage of fluocinolone is from approximately 0.001 to approximately 15 µg/day. In another embodiment, the dosage of fluocinolone is from approximately 0.001 to approximately 10 µg/day. In another embodiment, the dosage of fluocinolone is from approximately 0.001 to approximately 5 µg/day. In another embodiment, the dosage of fluocinolone is from approximately 0.001 to 2.5 µg/day. In some embodiments, the amount of fluocinolone is between 40 and 600 µg/day. In some embodiments, the amount of fluocinolone is between 200 and 400 µg/day. Dosing formulations may be prepared to contain a sufficient amount of the active ingredient to enable the desired about of compound to be release over the desired amount of time.

In some embodiments, there is sufficient fluocinolone such that the fluocinolone is released at a rate of 2-3 µg per day for a period of at least three days. In some embodiments, this release rate continues for, at least ten days, at least fifteen days, at least twenty-five days, at least thirty days, at least fifty days, at least ninety days, at least one hundred days, at least one-hundred and thirty-five days, at least one-hundred and fifty days, or at least one hundred and eighty days.

For some embodiments, 300-350 micrograms of fluocinolone as formulated with a biopolymer are implanted into a person at or near a target tissue site. If fluocinolone is implanted at multiple sites that triangulate the target site then in some embodiments, the total amount of fluocinolone at each site is a fraction of the total 300-350 micrograms. For example, one may implant a single does of 324 micrograms at one site, or two separate doses of 162 micrograms at two sites, or three separate dose of 108 micrograms at three sites that triangulate the tissue site. It is important to limit the total dosage to an amount less than that which would be harmful to the organism. However, in some embodiments, although when there are a plurality of sites each site may contain less than the total does that might have been administered in a single application, it is important to remember that each site will independent have a release profile, and the biopolymers' concentration and substance should be adjusted accordingly to ensure that the sustain release occurs over sufficient time.

In some embodiments, there is a drug depot comprising fluocinolone or fluocinolone and a polymer, wherein the polymer is one more of poly(lactide-co-glycolide) (PLGA), D-lactide, D,L-lactide, L-lactide, D,L-lactide-caprolactone, and D,L-lactide-glycolide-caprolactone.

In various embodiments, the bolus dose or burst effect lasts over 1, 2, 3, 4, or 5 days and the maintenance dose lasts longer (e.g., over 135 days daily doses of 0.02 mg of fluocinolone). In various embodiments, polymers capable of achieving this elution profile include polymers having a relatively high lactide/glycolide ratio (e.g. 85/15 PLGA; 90/10 PLGA; DL-PLA).

Having now generally described the invention, the same may be more readily understood through the following reference to the following examples, which are provided by way of illustration and are not intended to limit the present invention unless specified.

EXAMPLES

Certain abbreviations are used in the some of the tables and figures. The abbreviation. The abbreviations "DL" or "DL-PLA" refer to poly(DL-lactide). The abbreviation "PLGA" refers to poly(lactide-co-glycolide).

Often times when the polymer is a heteropolymer or copolymer, there is a mixture of monomer species in the polymer. The mole ratio may be indicated and varied from 0:100 to 100:0 and ranges in between these mole ratios. For example, 85:15 PLGA, the 85 refers to the monomer mole % 85 of DL (poly DL-lactide) in the polymer, while the 15 refers to the mole percent of the PGA (polyglycolide) in the polymer.

The codes within the table for the polymer are explained as follows. The first number or numbers refers to monomer mole percentage ratio of DL-lactide (e.g., polylactide) to glycolide (e.g., poly-glycolide). The letter code that follows the first number refers to the polymer(s) and is the polymer identifier. The second number, which follows the letter code for the polymer, is the target IV designator and is 10 times the midpoint of a range in dl/g. The meanings of certain IV designators is reflected in Table A below.

TABLE A

| IV Target Designator | IV Range |
| --- | --- |
| 1 | 0.05-0.15 |
| 1.5 | 0.10-0.20 |
| 2 | 0.15-0.25 |
| 2.5 | 0.20-0.30 |
| 3 | 0.25-0.35 |
| 3.5 | 0.30-0.40 |
| 4 | 0.35-0.45 |
| 4.5 | 0.40-0.50 |
| 5 | 0.45-0.55 |
| 6 | 0.50-0.70 |
| 7 | 0.60-0.80 |
| 8 | 0.70-0.90 |
| 9 | 0.80-1.0 |

The final letter within the code of the polymer is the end group designator. For examples "E" refers to an ester end group, while "A" refers to an acid end group.

The polymers may have different end groups such as acid and ester end groups. Implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., lauryl, methyl, and/or ethyl ester end groups).

By way of example, 100 DL 7E is a polymer that has an inherent viscosity of 0.60-0.80 dL/g. It contains 100% poly(DL-lactide) that has ester end groups. It is available from Lakeshore Biomaterials, Birmingham, Ala.

Example 1

FIG. 1 provides a table fourteen formulations that contain fluocinolone and excipients, including one formulation that contains no excipients. FIG. 2 provides a graph of a cumulative API released percentage for the formulations of FIG. 1, some of which have been irradiated. (Note that in the legend, the percentage of the FL (fluocinolone) is rounded off). FIG. 3 provides the calculated daily micrograms released for the last six formulations in FIG. 1.

The In-Vitro Elution Studies were carried out at 37° C. in phosphate-buffered saline with 0.5% SDS (pH 7.4). Briefly, the rods (n=3) were weighed prior to immersion in 10 mL of PBS. At regular time intervals, the PBS was removed for analysis and replaced with 10 mL of fresh PBS. The PBS-elution buffer was analyzed for fluocinolone content using UV-Vis spectrometry.

Example 2

Figure 5:
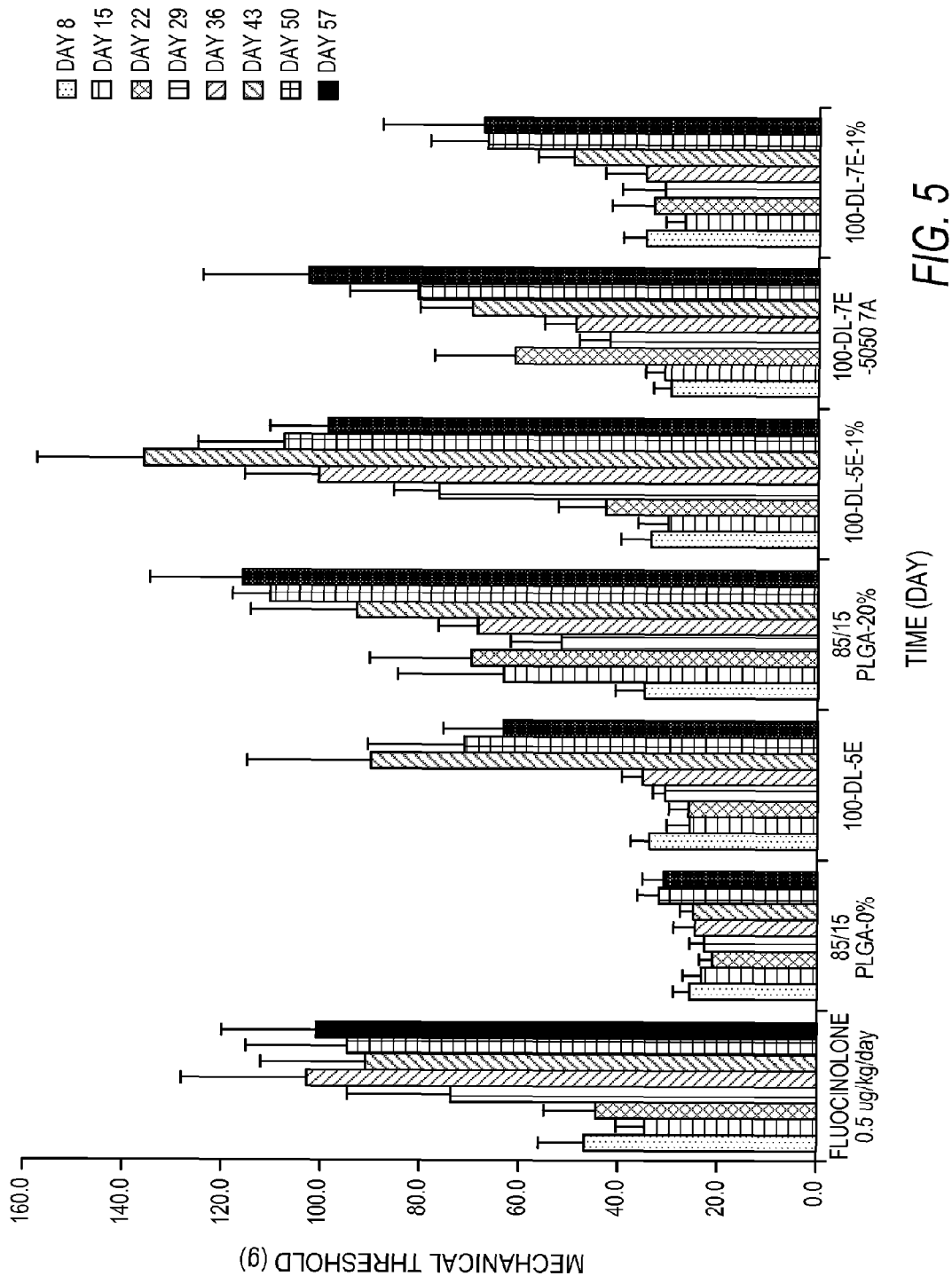
FIG. 5 is a bar graph that depicts the thermal paw withdrawal latency as a percentage from baseline for the following administrations: fluocinolone 0.5 µs/kg/day subcutaneously, 85/15 PLGA-0%, 100-DL-7E, 85/15 PLGA-20%, 100-DL-5E-1%, 100-DL-7E-5050 7A and 100-DL-7E-1% at 7 days, 14 days, 21 days, 28 days, 35 days, 42 days, 49 days, and 56 days.

A 2-month chronic constriction injury (CCI) model of neuropathic pain was used to evaluate different formulations of a corticosteroid, fluocinolone, encapsulated in bioerodable polymers compared to fluocinolone given subcutaneously (SC). Different formulations as provided in Table B below were evaluated for reducing pain-associated behaviors: Thermal paw withdrawal latency was evaluated at baseline 7, 14, 21, 28, 35, 42, 49, and 56 days post-operatively, while mechanical threshold was evaluated at 8, 15, 22, 29, 36, 43, 50, and 57 days post-operatively. Bar graphs depicting the results of theses tests are shown in FIGS. 4 and 5.

There were seven groups of animals tested. Each animal received treatment of test or control article according to the dosing groups (n=8) described in the Table A. Group 1 received daily drug injections. Groups 2-7 received solid, polymer implants that were implanted caudal to the CCI in a manner that totally surrounds the nerve.

TABLE B

| Group Number | Treatment | Dose | Comments |
|---|---|---|---|
| 1 | Fluocinolone | 0.5 ug/kg | Daily SC administration |
| 2 | 85/15 PLGA | 0% | control |
| 3 | 100 DL 5E + Glacial acetic acid/7% 5050 7A | 0% | control |
| 4 | 85/15 PLGA + 10% mPEG | 20% | 1 pellet |
| 5 | 100 DL 5E + 10% PEG1500 | 1% | 1 pellet |
| 6 | 100 DL 7E + 5% PEG/7% 5050 7A | 1% | 1 pellet |
| 7 | 100 DL 7E + 10% PEG1500 | 1% | 1 pellet |

Mechanical allodynia was measured using von Frey monofilaments (Stoelting, Wood Dale, Ill.) with varying stiffness (2.0-15.0 g) on Days 1, 8, 15, 22, 29, 36, 43, 50 and 57 as described previously (see FIGS. 5-6). Animals were placed on a perforated metallic platform and allowed to habituate to their surroundings for a minimum of 15 minutes before testing. The 50% paw withdrawal threshold response was determined by a sequential increasing and/or decreasing of the stimulus strength (the "up-down method" of Dixon). Each filament was applied with enough pressure to cause a buckling effect. Absence of a paw lifting/withdrawal response after 5 seconds prompted the use of the filament of next higher weight. Paw withdrawal indicating a positive response prompted the use of a weaker filament. After the initial response (i.e., paw withdrawal), the testing continued for four additional measurements and was used to calculate the response threshold. Four consecutive positive responses received a score of 0.25 g, and five consecutive negative responses (i.e., no paw withdrawal) received a score of 15 g. The 50% paw withdrawal threshold was calculated using the formula: $10(X_f+kd)/10,000$, where $X_f$ is the final von Frey filament used (log units), k is a value that analyzes the response pattern (taken from the table published by Chaplan et al.), and d is the mean difference between stimuli (log units). The mean and standard error of the mean (SEM) were determined for each treatment group.

The data are graphically represented in FIGS. 4 and 5, which show that fluocinolone drug depots were effective at reducing pain and/or inflammation when compared to the control (unloaded polymer depots) for at least 57 days.

Example 3

Fluocinolone Formulations and Release Profiles

Fluocinolone is a potent steroid with glucocorticoid activity. To get consistent release additional excipients were added to the polymer formulation. For example with drug loads of 1% to 20% fluocinolone, 85/15 PLGA or DL-PLA or DL-PLA and 50/50 PLGA mixture can be added in an amount of from about 10% to 98%. The depot can be extruded and made into different sizes (e.g., 0.75 (length)× 0.75 mm (diameter), 0.8×0.8 mm, 1×1 mm pellet sizes).

Figure 6:
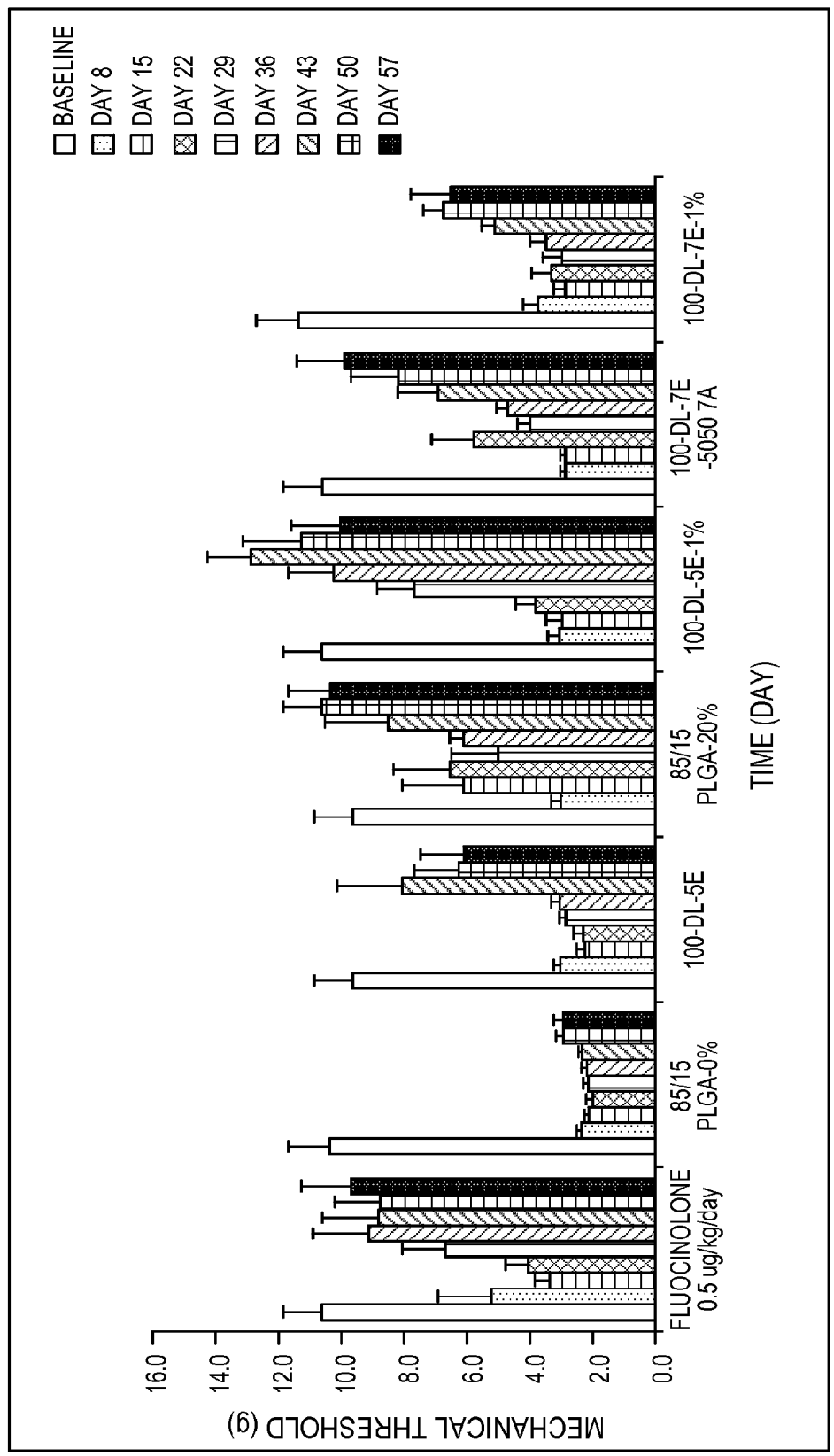
FIG. 6 is a table of a number of fluocinolone formulations.
Figure 7:
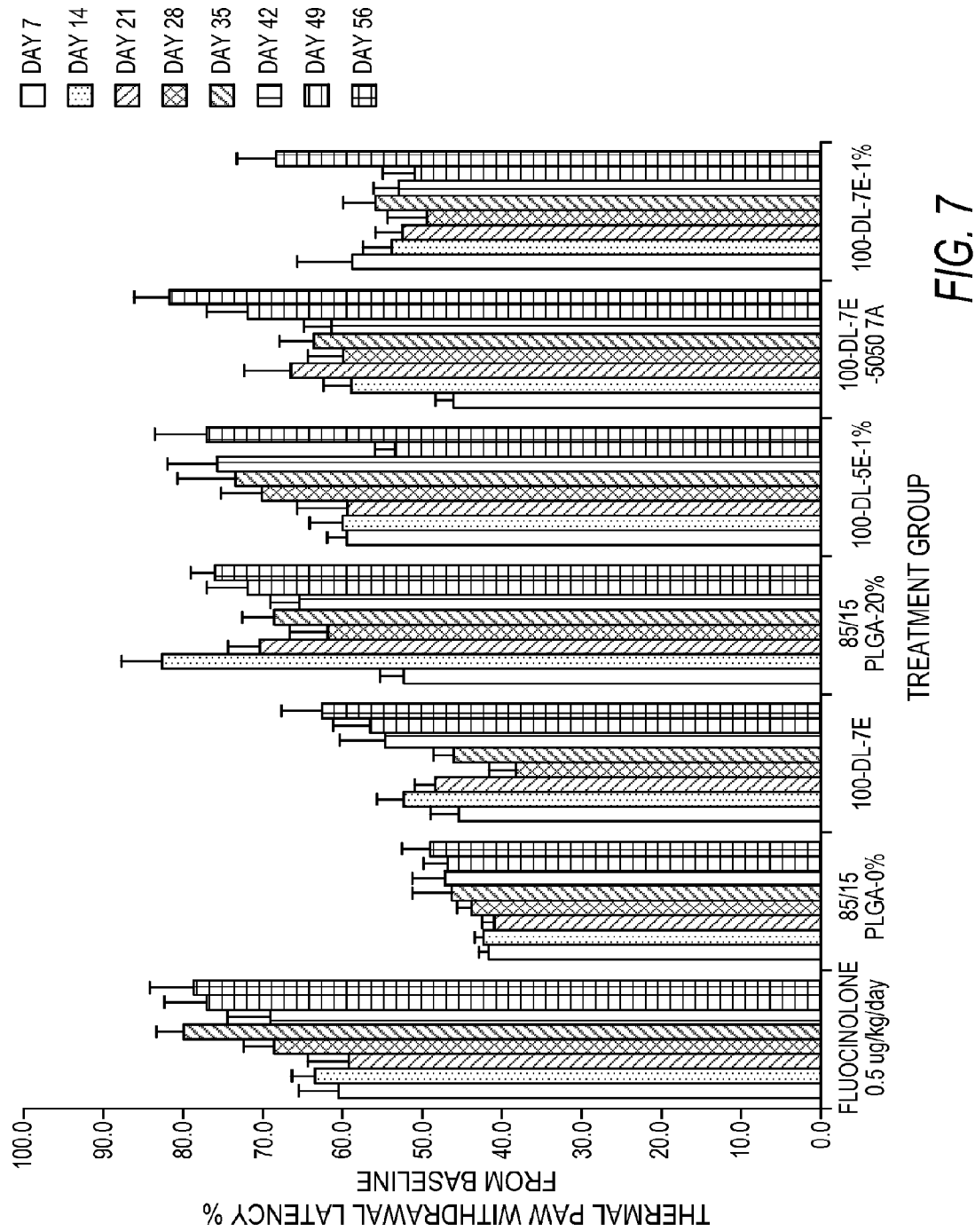
FIG. 7 is a set of four graphs that depict in vitro elution data for a number of fluocinolone formulations.

FIG. 6, Table C shows the various fluocinolone formulations made and some of their elution profiles ranging from 38 days to 100 days with fluocinolone release rates of 0% to 60% cumulative release shown in FIGS. 7 and 8. This type of release profile would be beneficial in reducing, treating or preventing pain and/or inflammation or tissue or organ transplant rejection.

Figure 9:
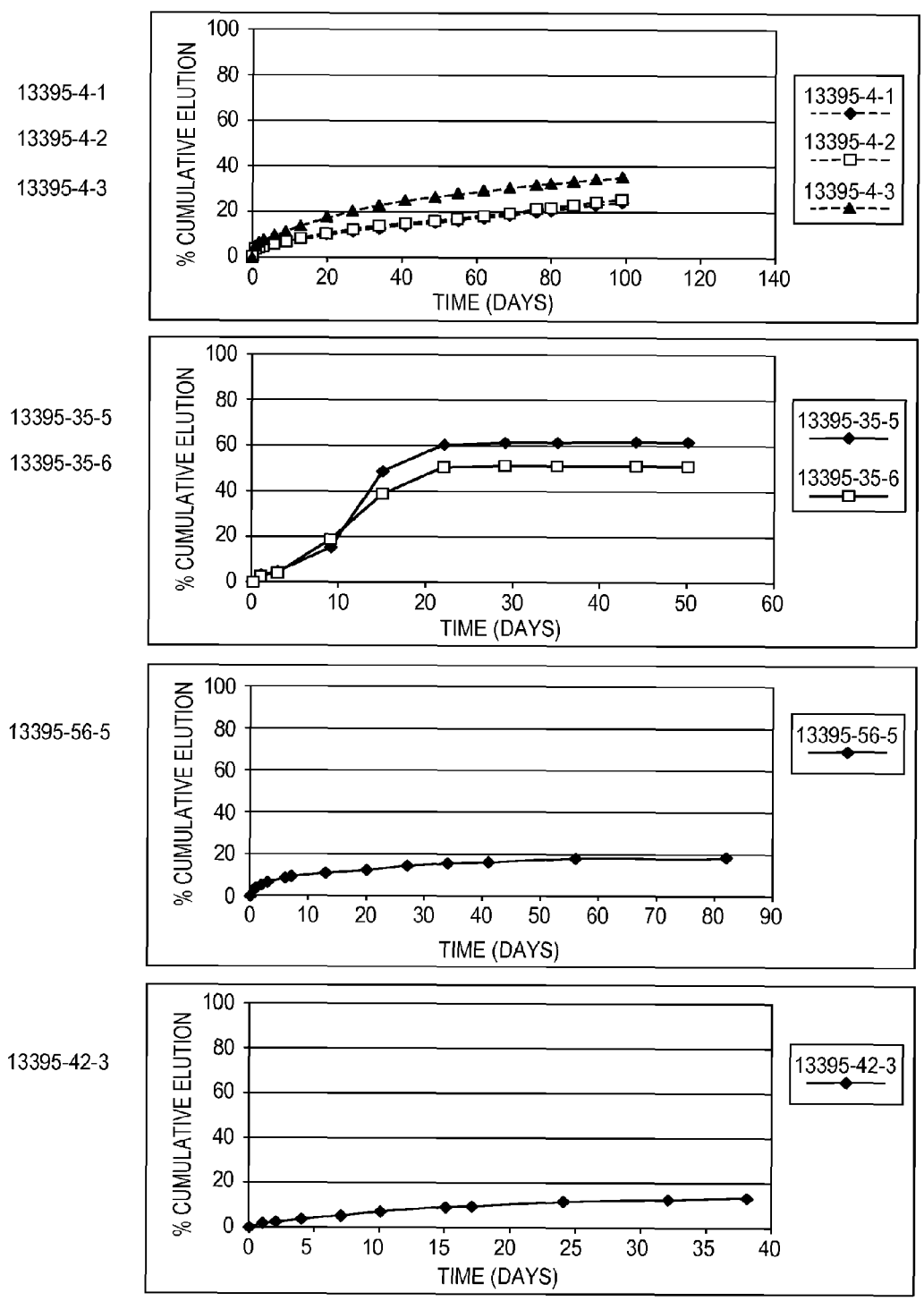
FIG. 9 is a picture of an NSAID (sulindac) with a very similar pain control response, but it did not prevent encapsulation, and the sutures were resorbed.

FIG. 10 is a picture of fluocinolone implants 20 wt % 85/15 PLGA+10% mPEG and 1% wt fluocinolone 100 DL 7E+5% PEG/7% 50/50 PLGA 7A. The foreign and inflammatory material was not resorbed due to lack of inflammatory response mediated by fluocinolone implants. There was also no encapsulation due to attachment of cells such as fibroblasts. FIG. 9 is a picture of an NSAID (sulindac) with a very similar pain control response, but did not prevent encapsulation, and the sutures were resorbed.

A test was conducted to determine if fluocinolone was toxic to human cells. The cell line tested was human smooth muscle vascular cells. The results indicated that fluocinolone was not toxic to these cell types.

Example 4

Purpose:

The purpose of these studies were to evaluate the in vivo drug elution rate from a biodegradable polymer dosage form and compare it to previously generated in vitro data.

Experimental Methods Summary:

Twenty four Sprague Dawley rats were utilized in this study. Every rat was implanted with two or three subcutaneous (SQ) implants (2 sites per animal). Group 1 received active-loaded polymer. Group 2 received unloaded (control) polymer (3 sites per animal).

The polymer pellets were implanted by making a dorsal midline skin incision (approximately 2 cm long) and creating a lateral SQ pocket (approximately 1 cm×1 cm) by blunt dissection. The pellets were deposited with a forceps. The skin incision was closed using skin staples.

The rats were allowed to recover from the implant procedure, and sacrificed on Days 3, 7, 14, 21, 28, and 66 according to a predetermined schedule. At necropsy, the remaining dosage form was identified, and some portion was recovered. The retrieved portion of the dosage form was weighed and analyzed for drug content. At termination, a blood sample was collected via cardiac puncture (approximately 1 mL) and transferred to an EDTA tube. Plasma in EDTA was isolated for future drug analysis. Table D summarizes the fluocinolone depots used and the test parameters.

TABLE D

| Gp | Strain of Rat | Formal ID | Dosage Form | Pellet #r | Pellet Dimensions (L × D) (mm) | # of Test Sites per Animal | # of Sacrifices | Animal Sacrifices[a] | Total # of Animals |
|---|---|---|---|---|---|---|---|---|---|
| 1 | N | 13395-63-6 | *20% Fluoc in. in 85/15 PLG A + 10% mPE G | 6 | 0.7 × 0.7 | 2 | 6 | 3 | 18 |
| 2 | N | 13395-68-5 | 85/15 PLG A + 10% mPE G | 6 | 4 × 0.75 | 3 | 2 | 3 | 6 |

N = normal ~300 g Spague-Dawley
[a]Group 1 was sacrificed at: 3, 7, 14, 21, 28, and 56 days post-implant (Implant = Day 0)
Group 2 was sacrificed at: 28 and 56 days post-implant (Implant = Day 0)

Figure 11:
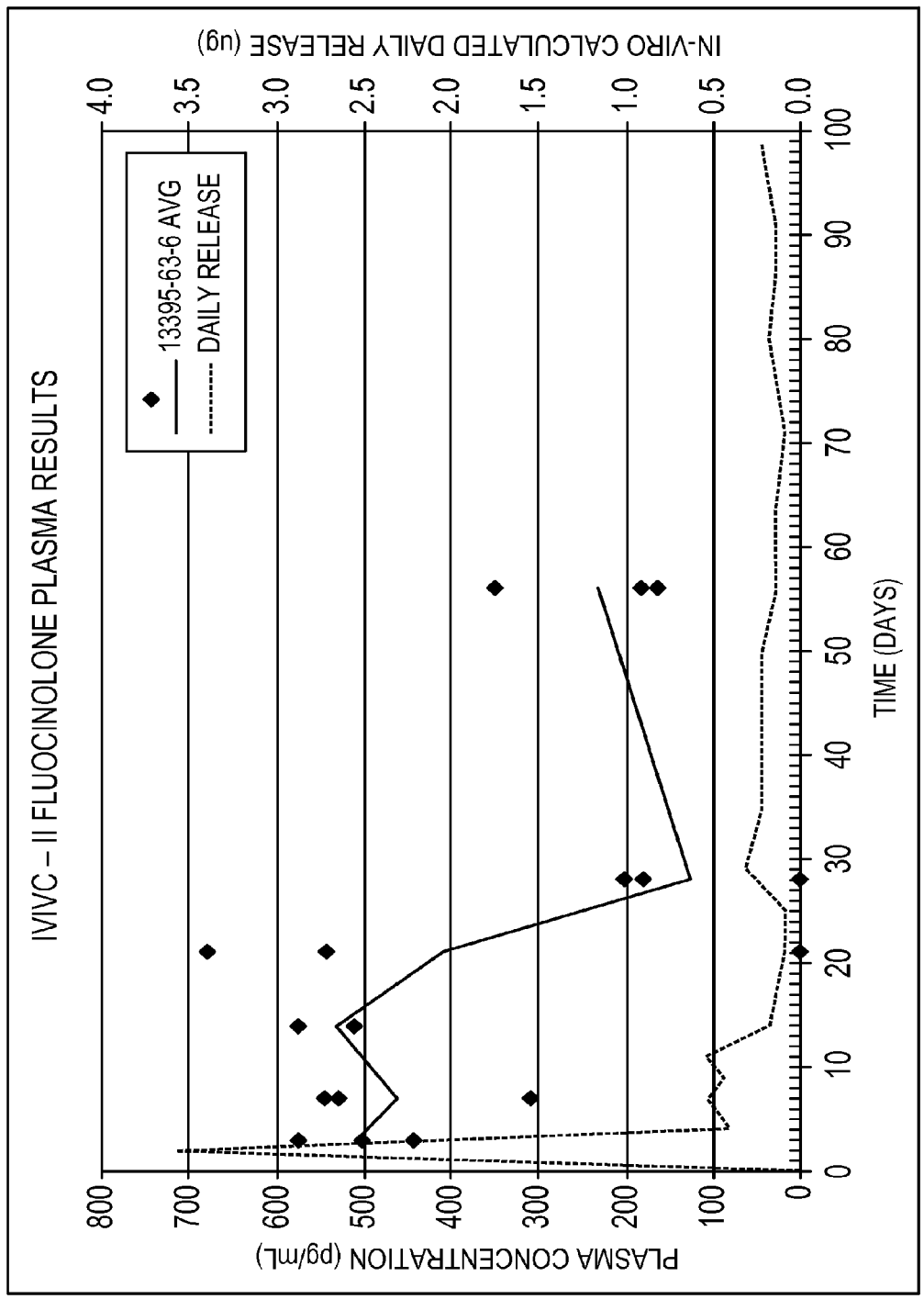
FIG. 11 shows in vivo plasma serum levels and in vitro elution profiles for exemplary fluocinolone formulations.

FIG. 11 shows in vitro daily release profiles and in vivo daily plasma level profiles of 12 depots (6 depots implanted in two sites) containing fluocinolone. This dosage is approximately double the amount of normal human doses (6 depots would be used in humans). An initial burst or immediate release of fluocinolone was observed for about 3 days, achieving over 1.5 to over 3.5 mcg per day for the in vitro testing. The in vivo plasma levels had an initial burst in about 3 days of about 400-600 pg/ml in the plasma, which is relatively low considering 12 depots were implanted. After about 3 days, an in vitro daily drug release from the depots was between about 0.01 and about 2.5 mcg/day in a consistent release for over 100 days. The in vivo plasma levels of fluocinolone were also consistent after 30 days achieving plasma levels in the 150 to 250 picograms/ml range.

The following fluocinolone formulation was prepared in Table E.

IVIVC-2 Study Table E Fluocinolone Content Purity and Results
Group 5: Fluocinolone 20%: 70% PLGA 8515: 10% mPEG

| Formulation | Ave Dose Wt. 5 Pellets (mg) | Drug Content mcg/ pellet | Content Uniformity | % Drug Load | % Theoretical | Drug Purity % Peak Area |
|---|---|---|---|---|---|---|
| Pre-Sterile | 3.14 | 625 | 10.4% | 19.9% | 99.5% | 99.0% |
| Post-Gamma | 3.11 | 612 | 13.9% | 19.7% | 98.4% | 98.9% |

Figure 12:
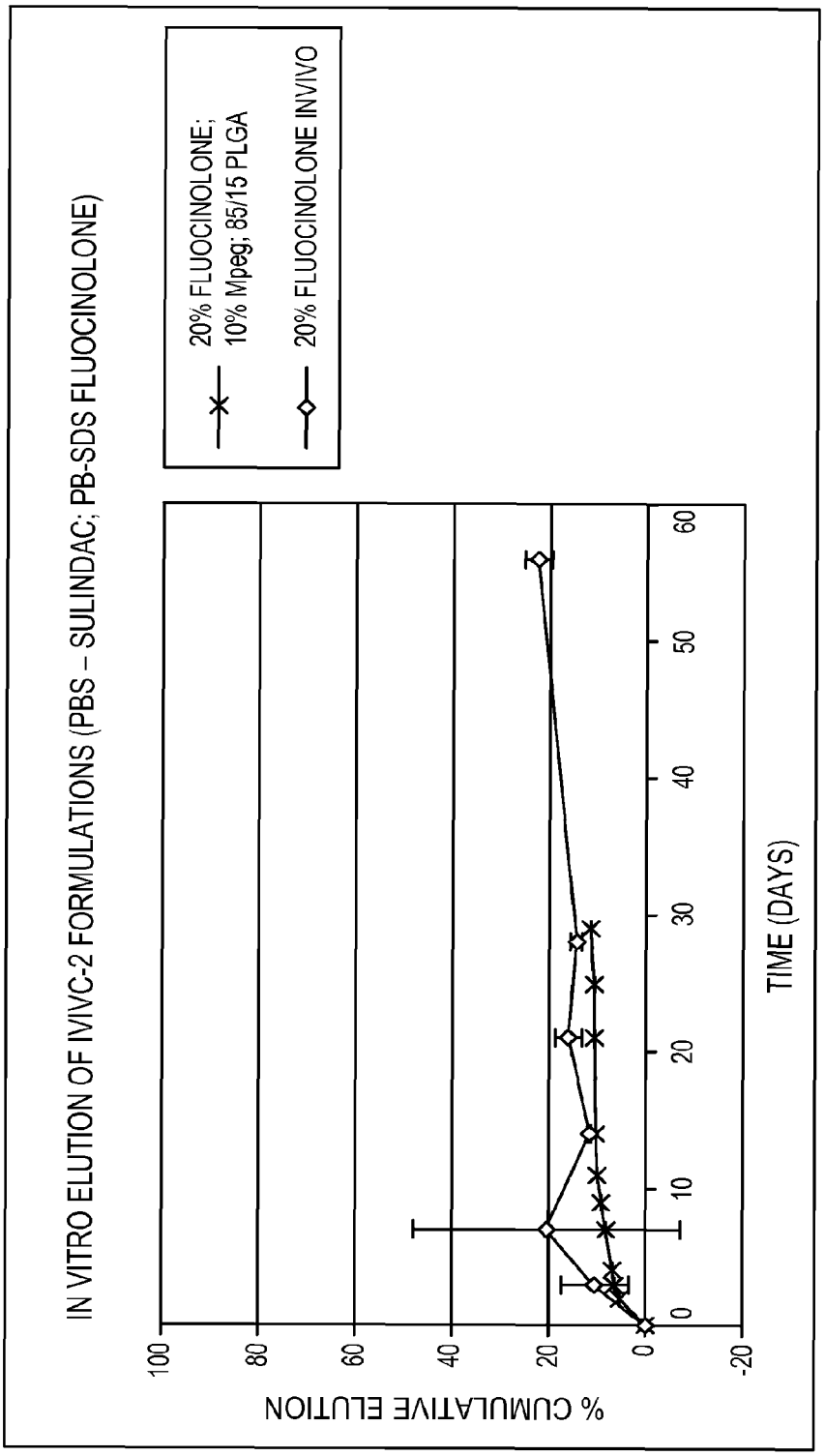
FIG. 12 shows in vitro elution profiles and in vivo plasma serum levels for exemplary fluocinolone formulations.

The elution profiles for the pellets in Table E are shown in FIG. 12. The fluocinolone drug depot had about 20% to 25% of fluocinolone eluted from the depot in vivo for a period of 30 days. In vivo drug depots were measured by explanting the pellet and measuring the wt % drug eluted from the depot. In vitro drug elution was measured using PBS or PBS and SDS and measuring the wt % cumulative elution. The in vitro elution correlated with in vivo elution where there was an initial burst effect and immediate release of the drug within the first 3 days and then a consistent sustained release for up to 57 days or 30 days, respectively.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of reducing or treating pain, wherein said method comprises implanting a drug depot at a target tissue site beneath the skin of a patient, wherein said drug depot comprises fluocinolone in an amount from about 0.05 wt. % to about 25 wt. % of the drug depot, and a biodegradable polymer comprising poly(lactide-co-glycolide) (PLGA) having an inherent viscosity of 0.6 dL/g to 0.8 dL/g, and the drug depot has a modulus of elasticity from about $2\times10^5$ dynes/cm$^2$ to about $5\times10^5$ dynes/cm$^2$, and the drug depot has a surface that releases a burst dose of the fluocinolone in an amount of 0.001 μg to 5 μg within 24 hours at the target tissue site, and the drug depot releases an effective amount of the fluocinolone over a period of at least fifty days, and the drug depot has a particle size from about 10 to about 200 micrometers, and the drug depot further comprises mPEG.

2. A method according to claim 1, wherein said fluocinolone comprises from about 1 wt. % to about 15 wt. % of the drug depot.

3. A method according to claim 1, wherein said biodegradable polymer comprises at least 80 wt. % of the drug depot.

4. A method according to claim 1, wherein the at least one biodegradable polymer comprises poly(lactic-co-glycolic acid) and said poly(lactic-co-glycolic acid) comprises a mixture of polyglycolide and polylactide.

5. A method according to claim 4, wherein said mixture comprises more polylactide than polyglycolide.

6. A method according to claim 1, wherein said implanting comprises applying said drug depot at a plurality of sites that triangulate a pain generator.

7. A method according to claim 1, wherein the drug depot further comprises one or more viscosity enhancing agents comprising hydroxypropyl cellulose, hydroxypropyl methylcellulose, hydroxyethyl methylcellulose, carboxymethylcellulose, carbopol, polyhydroxyethylmethacrylate, poly(methoxyethylmethacrylate), poly(methoxyethoxyethylmethacrylate), PMMA, MMA, gelatin or a combination thereof.

* * * * *